United States Patent
Dimitroulis

(10) Patent No.: US 11,491,012 B2
(45) Date of Patent: Nov. 8, 2022

(54) PROCEDURE AND ORBITAL IMPLANT FOR ORBIT ANCHORED BONE AFFIXATION OF AN EYE PROSTHESIS

(71) Applicant: TMJ ORTHOPAEDICS PTY LTD, East Melbourne (AU)

(72) Inventor: George Dimitroulis, East Melbourne (AU)

(73) Assignee: TMJ ORTHOPAEDICS PTY LTD, East Melbourne (AU)

( * ) Notice: Subject to any disclaimer, the term of this patent is extended or adjusted under 35 U.S.C. 154(b) by 290 days.

(21) Appl. No.: 16/981,642

(22) PCT Filed: Apr. 4, 2019

(86) PCT No.: PCT/AU2019/050290
§ 371 (c)(1),
(2) Date: Sep. 16, 2020

(87) PCT Pub. No.: WO2019/191805
PCT Pub. Date: Oct. 10, 2019

(65) Prior Publication Data
US 2021/0106424 A1    Apr. 15, 2021

(30) Foreign Application Priority Data

Apr. 4, 2018  (AU) ............................... 2018901100

(51) Int. Cl.
*A61F 2/28*  (2006.01)
*A61F 2/14*  (2006.01)
*A61F 2/30*  (2006.01)

(52) U.S. Cl.
CPC ............ *A61F 2/2875* (2013.01); *A61F 2/141* (2013.01); *A61F 2002/2878* (2013.01);
(Continued)

(58) Field of Classification Search
CPC ............ A61F 2/2875; A61F 2002/2878; A61F 2002/2882; A61F 2002/2885;
(Continued)

(56) References Cited

U.S. PATENT DOCUMENTS 5,064,374 A * 11/1991 Lundgren ............ A61C 8/0048
                                                        433/213
5,263,980 A * 11/1993 Leibinger ................ A61F 2/00
                                                        433/172

(Continued)

FOREIGN PATENT DOCUMENTS

FR    2806630 A1    9/2001

OTHER PUBLICATIONS

International Search Report dated May 13, 2019 from PCT Application No. PCT/AU2019/050290.

*Primary Examiner* — Alvin J Stewart
(74) *Attorney, Agent, or Firm* — Innovation Capital Law Group, LLP; Vic Lin

(57) ABSTRACT

An orbital implant adapted for attachment to the very thin bone at the orbit rim (502), such as the zygomatic and frontal bone margin at the supero-lateral aspect (501) of the orbit (503), for the attachment of an eye prosthesis directly to distal ends of inwardly convergently orientated transdermal abutments. The orbital implant has a baseplate (100) having an orbit radius curvature and an orbit rim curvature and a plurality of microfixation apertures therethrough and the plurality of transdermal abutments are located at an inner edge of the baseplate (100).

28 Claims, 5 Drawing Sheets

(52) U.S. Cl.
CPC .............. *A61F 2002/30952* (2013.01); *A61F 2220/0008* (2013.01); *A61F 2310/00023* (2013.01)

(58) Field of Classification Search
CPC .............. A61F 2002/2889; A61F 2/141; A61F 2/30942; A61F 2002/30952
See application file for complete search history.

(56) References Cited

U.S. PATENT DOCUMENTS

| | | | | |
|---|---|---|---|---|
| 5,593,444 | A * | 1/1997 | Svensson | A61F 2/141 623/17.17 |
| 5,697,979 | A * | 12/1997 | Pignataro | A61B 17/8605 606/187 |
| 5,743,913 | A * | 4/1998 | Wellisz | A61L 31/10 606/285 |
| 5,752,958 | A * | 5/1998 | Wellisz | A61B 17/8085 606/280 |
| 5,951,602 | A * | 9/1999 | Eaton | A61F 2/141 623/10 |
| 5,954,769 | A * | 9/1999 | Rosenlicht | A61B 17/1739 433/76 |
| 6,096,079 | A * | 8/2000 | Eaton | A61B 17/6433 606/53 |
| 7,787,934 | B2 * | 8/2010 | Mazzocchi | A61B 90/39 600/414 |
| 11,364,113 | B2 * | 6/2022 | Dimitroulis | A61F 2/2875 |
| 2002/0002402 | A1 | 1/2002 | Tse | |
| 2015/0105858 | A1 * | 4/2015 | Papay | A61L 27/18 623/11.11 |
| 2018/0344464 | A1 * | 12/2018 | Engstrand | A61B 17/8085 |
| 2020/0100894 | A1 * | 4/2020 | Woodburn, Sr. | A61F 9/007 |
| 2022/0031460 | A1 * | 2/2022 | Götz | A61F 2/2875 |
| 2022/0202575 | A1 * | 6/2022 | Noble | A61B 17/86 |

* cited by examiner

PROCEDURE AND ORBITAL IMPLANT FOR ORBIT ANCHORED BONE AFFIXATION OF AN EYE PROSTHESIS

FIELD OF THE INVENTION

This invention relates generally to a procedure and orbital implant for orbit anchored bone affixation of an eye prosthesis.

BACKGROUND OF THE INVENTION

Trauma, disease and developmental deformities may result in the loss of the eyeball, eyelids or surrounding muscles of the eye. A missing eye results in loss of binocular vision and hence depth perception. Aesthetic and psychological stigma of a missing eye may lead to social seclusion and depression.

Currently, facial prosthetic laboratories fabricate life-like glass eyes with surrounding eyelids of silicon rubber which can be held in place with a modified pair of spectacles. Unfortunately, spectacles have problems of micro-movement and skin irritation.

As such, alternative arrangements may comprises a stand-alone orbital prosthesis that is directly anchored to the underlying facial bone with miniature osseointegrated titanium screws.

However, because the bone thickness at the orbit rim is very thin, the screws must be extremely short or placed more securely elsewhere. Also, the placement of the screws is often reliant on guess work.

Furthermore, the screws must be left in place for 3 to 6 months to integrate before a second surgery is used to re-expose the screws to attach transdermal healing abutments. As such, construction of the prosthetic eye can only commence once the healing abutments are in place and so the patient has to wait a further 2-3 weeks before the final prosthetic eye is ready to attach to the implants.

To counter disadvantages of unfavourable marginal conditions (i.e. that implants cannot always be ideally placed for ideal mounting of the artificial body part), U.S. Pat. No. 5,263,980 A (LEIBINGER et al.) 23 Nov. 1993 [hereinafter referred to as D1] discloses a securing artificial body parts such as ears, noses and eyes, to a planar grid. Transdermal posts extend from the grid which have caps which holds wire webbing to which an artificial body part can be secured by means of a clamp, clip or the like.

As such, according to D1, implants can be secured away from unfavourable marginal conditions while allowing the ideal location of prosthesis by wire-form attachment to the various transdermal posts exposed from the grid of D1.

The present invention seeks to provide a procedure and orbital implant for orbit anchored bone affixation of an eye prosthesis, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein an orbital implant specifically adapted for attachment to the very thin bone at the orbit rim, such as the zygomatic and frontal bone margin at the supero-lateral aspect of the orbit, for the attachment of an eye prosthesis directly to distal ends of inwardly convergently orientated transdermal abutments, unlike the arrangement of D1 which teaches screw affixation away from such unfavourable marginal conditions and prosthesis affixation to a grid, post and wire scaffolding spanning therebetween.

As such, there is provided herein an orbital implant which has a baseplate having an orbit radius curvature and an orbit rim curvature and comprising a plurality of microfixation apertures therethrough and a plurality of transdermal abutments located at an inner edge of the baseplate.

As such, the present orbital implant attaches conformingly and discreetly directly to the orbit rim (such as the supero-lateral aspect of the orbit at the zygomatic and frontal bone margin) such that the transdermal abutments orientate convergently in towards the orbit from an inner edge of the baseplate. A prosthetic eye is then attached at a circumferential edge thereof to each of the inwardly convergent transdermal abutments by magnets, clips or screws or the like to securely and discreetly locate the prosthetic eye within the orbit.

As such, the present invention allows direct (i.e. without a wire scaffold as is taught by D1) and secure attachment of the baseplate to the very thin zygomatic and frontal bone margin at the supero-lateral aspect of the orbit (a region hitherto considered unfavourable by the prior art such as D1).

Furthermore, the inwardly convergent transdermal abutments allow for a compact and discreet direct attachment of the prosthetic eye, unlike the arrangement of D1 wherein the posts extend obtrusively perpendicularly from the face and which comprises an unsightly wire framework spanning therebetween necessitating coverage by larger and therefore less discreet prosthesis.

In a preferred embodiment, the prosthetic eye is securely held along a circumference thereof by a minimum number of inwardly convergent transdermal abutments, but preferably more than two transdermal abutments to prevent rotation of the prosthetic eye therebetween. As such, in a preferred embodiment the prosthetic eye is held at a circumferential edge thereof by just three inwardly convergent transdermal abutments which minimises transdermal trauma but which prevent rotation of the eye prosthesis.

As such, because the prior art such as D1 teaches screw affixation away from unfavourable bone margins and accurate placement of prosthesis with a planar grid, perpendicular post and wire web arrangement spanning therebetween, the prior art does not obviously suggest (and in fact teaches away from) the present orbital implant which is specifically designed for attachment directly to such "unfavourable" thin bone margins, such as the very thin zygomatic and frontal bone margin at the supero-lateral aspect of the orbit, in that the present microfixation perforated baseplate has an orbit radius curvature and an orbit rim curvature and a plurality of transdermal abutments convergently orientated from at an inner edge thereof such that the baseplate can be attached directly to the orbit rim and an eye prosthesis can be attached directly from distal ends of the convergently orientated transdermal abutments along a circumference thereof.

The present baseplate may be patient-specifically formed according to the actual profile of the patient's orbital rim obtained by CT scanning technique or the like. The position of the (preferably three) transdermal abutments arising from the baseplate may be determined by the position and shape of the orbital rim.

During the design phase, the present orbital implant may be digitally positioned against the orbital rim depicted by the CT scans. Once the orbital implant is properly positioned, usually in the supero-lateral aspect of the orbit, the baseplate may be digitally contoured to the orbital rim so that the baseplate lies flush with the bone. The orbital implant may then be 3-D printed in medical grade titanium. The abutments may be polished but the baseplate may be left rough to allow for osseointegration with the underlying bone and attachment of the overlying soft tissues.

Before the surgery, a 3-D printed bio model may be made of the patient's skull with a replica of the attached orbital implant attached so a prosthetist can use the bio model and replica attached thereto to construct the eye prosthesis which is finished and ready to attach to the orbital implant at the time of surgery.

To surgically install the orbital implant, the patient may be placed under general anaesthesia whereafter a semicircular incision may be made through the skin around the orbital rim to expose the underlying bone rim and adjacent orbital walls. The orbital implant may then be carefully positioned directly to the bony orbital rim according to the bony contours and the customised contouring of the baseplate of the implant.

The implant may secured directly to the skull bone with about 6-10 titanium micro screws that fit through the holes in the baseplate.

The surrounding skin may then be used to completely cover the base plate of the implant with only the (preferably three) polished transdermal abutments left protruding through the skin incision after the incision is closed with interrupted sutures.

Magnets, clips or even a titanium bar superstructure may then then be screwed onto the three protruding abutments and finally the eye prosthetic is attached to the orbital implant at the same surgery. The patient wakes up from their general anaesthetic with their new bone-anchored prosthetic eye.

As such, using 3-D print technology as well as computer aided design and manufacture (CAD-CAM), the orbital implant reduces or eliminates guesswork in proper positioning of a new eye prosthesis. Furthermore, a digitally designed and manufactured custom orbital implant allows a prosthetist to construct an eye prosthesis to a high level of accuracy before surgery such that eye prosthesis can be attached at the time of surgery, eliminating the conventional three stage process of two surgical procedures and a third step of impressions for manufacture of the prosthetic eye.

Rather, the present techniques may allow for an all-in-one procedure where the titanium orbital implant, including a titanium bar superstructure if required, as well as the prosthetic eye are attached together in one operation.

Furthermore a bone anchored eye prosthesis avoids patients having to rely on spectacles to support the prosthesis and provides securer attachment, ultimately offering the patient greater when social interactions confidence.

According to one aspect, there is provided a procedure for orbit anchored bone affixation of an eye prosthesis, the providing comprising: providing an orbital implant, the orbital implant comprising: a baseplate having an orbit radius curvature and an orbit rim curvature and comprising a plurality of microfixation apertures therethrough; and a plurality of transdermal abutments convergently orientated from at an inner edge of the baseplate; making an incision to expose a rim of the orbit; attaching the baseplate to the rim; securing the baseplate using a plurality of microfixation screws located through microfixation respective apertures; closing the incision to cover the baseplate while leaving the transdermal abutments exposed; and affixing the eye prosthesis to the transdermal abutments.

The base plate may comprise a major anterior portion and at least one minor medial/posterior portion, the at least one minor medial/posterior portion extending posteriorly from an inner edge of the major anterior portion.

The microfixation apertures may be predominantly located through the major anterior portion.

The at least one minor medial/posterior portion may be located at a respective transdermal abutment.

The at least one minor medial/posterior portion may be at least one of absent or recessed at locations between adjacent transdermal abutments.

The method may comprise affixing between 5 and 11 microfixation screws.

The plurality of transdermal abutments may stand substantially perpendicularly from the inner edge so as to be inwardly convergently orientated.

The procedure may comprise attaching the baseplate at a supero-lateral edge of the orbit between the zygomatic and frontal bones.

The procedure may further comprise obtaining patient geometry and CAD modelling to adjust the shape of the baseplate in conformance with the patient geometry.

CAD modelling may further comprise adjusting positioning of the at least one transdermal abutment according to the patient geometry.

The procedure may further comprise generating a physical biomodel of the orbit and generating the implant or a replica thereof and constructing an eye prosthesis with reference to physical handling of the physical bio model and the implant or the replica thereof.

The procedure may further comprise attaching connectors to the transdermal abutments and attaching the prosthesis using the connectors.

The eye prosthesis may comprise a plurality of attachments along a circumference thereof which correspond in location to distal ends of the transdermal abutments.

The transdermal abutments may comprise more than two transdermal abutments.

The transdermal abutments may comprise three transdermal abutments.

The connectors may be releasable connectors for releasable connection of the prosthesis.

The connectors may comprise magnetic connectors.

According to another aspect, there is provided apparatus comprising an orbital implant for bone anchored affixation of an eye prosthesis, the implant comprising: a baseplate having an orbit radius curvature and an orbit rim curvature and comprising a plurality of microfixation apertures therethrough; and a plurality of transdermal abutments convergently orientated from at an inner edge of the baseplate.

The base plate may comprise a major anterior portion and at least one minor medial/posterior portion, the at least one minor medial/posterior portion extending posteriorly from an inner edge of the major anterior portion.

The microfixation apertures may be predominantly located through the major anterior portion.

The at least one minor medial/posterior portion may be located at a respective transdermal abutment.

The at least one minor medial/posterior portion may be at least one of absent or recessed at locations between adjacent transdermal abutments.

The plurality of transdermal abutments may stand substantially perpendicularly from the inner edge and orientated inwardly towards the orbit.

The transdermal abutments may be substantially respectively orientated towards a point of convergence within the orbit.

The transdermal abutments may comprise more than two transdermal abutments.

The transdermal abutments may comprise three transdermal abutments.

The apparatus may further comprise a spherical eye prosthesis comprising a plurality of attachments along a circumference thereof and wherein the plurality of attachments correspond in location to distal ends of the plurality of transdermal abutments.

The distal ends of the plurality of transdermal abutments and the attachments may magnetically attract.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
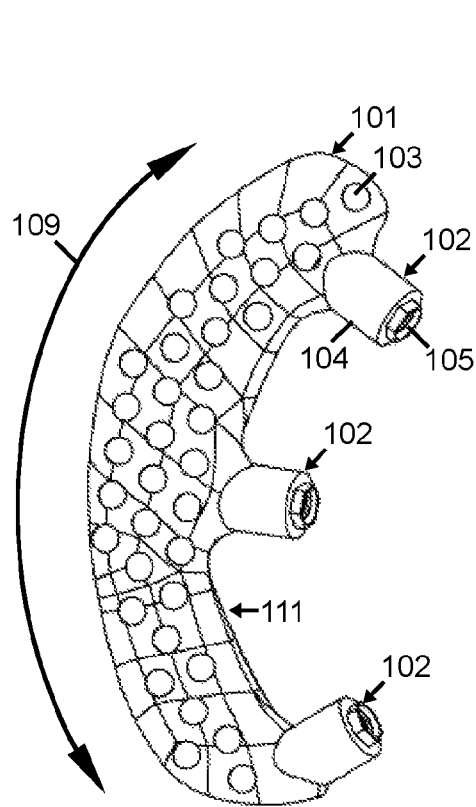
FIG. 1 shows a top perspective view of an orbital implant for orbit attachment affixation of an eye prosthesis in accordance with an embodiment.
Figure 2:
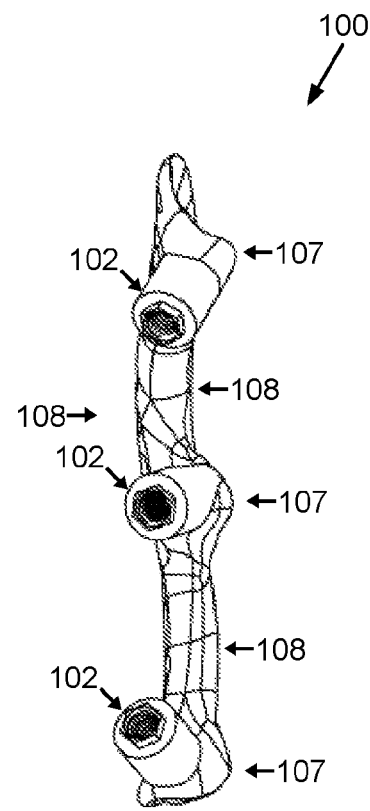
FIG. 2 shows an inner edge-on perspective view of the implant.
Figure 3:
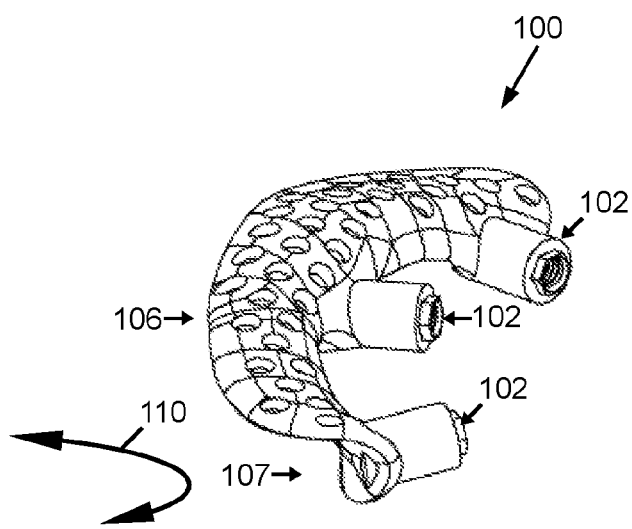
FIG. 3 shows an end-on perspective view of the implant.
Figure 4:
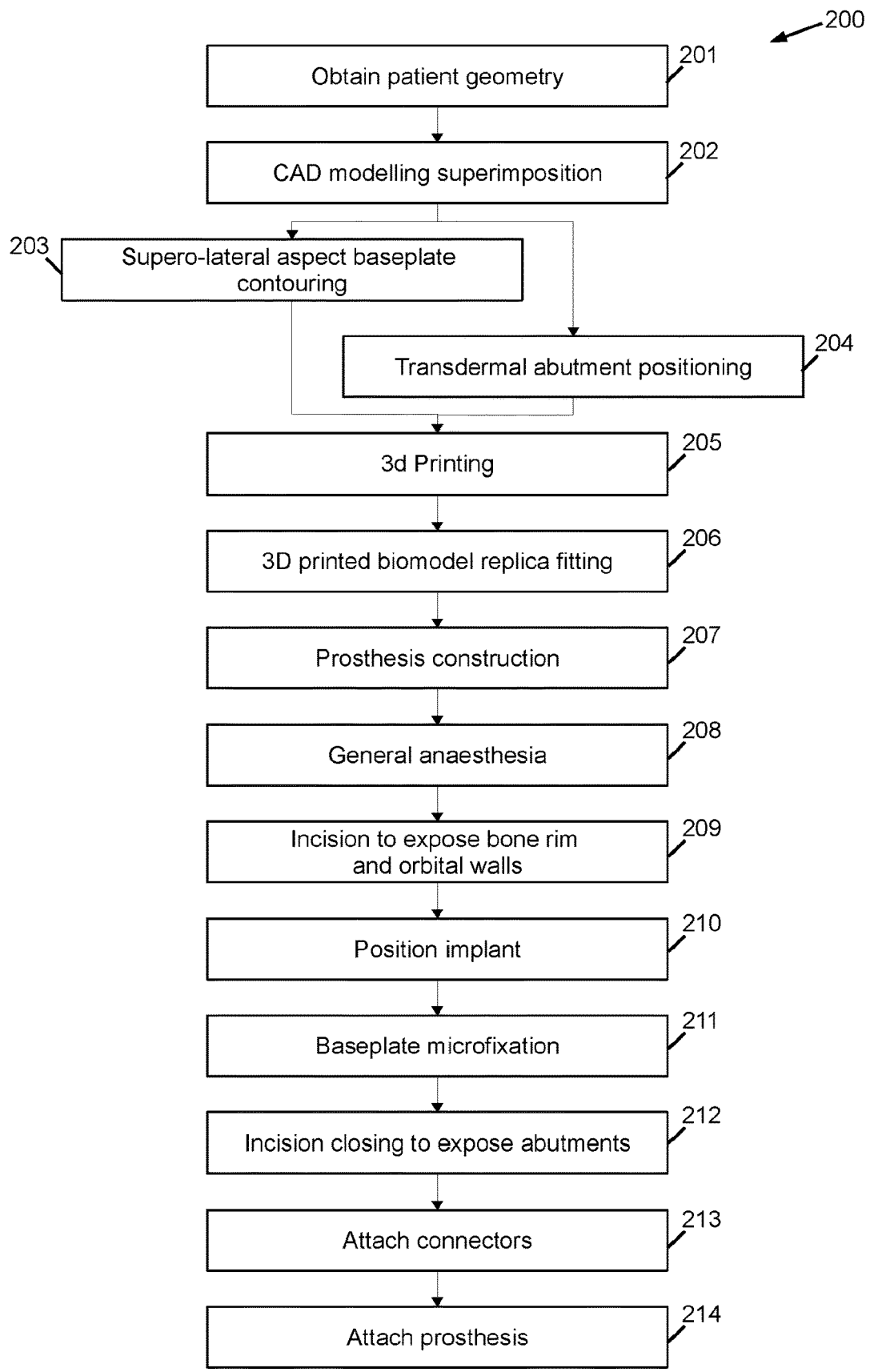
FIG. 4 illustrates an exemplary procedure for orbit anchored bone affixation of an eye prosthesis using the implant in accordance with an embodiment.

FIGS. 1-3 show an orbital implant 100 for bone anchored affixation of an eye prosthesis.

The implant 100 comprises a base plate 101, preferably of resilient biocompatible material, such as titanium.

The baseplate 101 is shaped to comprise an orbital radius curvature 109 and an orbit rim curvature 110 so as to conform to the bone of the rim an adjacent wall of the orbit for affixation thereto in the manner described herein.

The baseplate 101 may comprise a plurality of microfixation apertures 103 which may be substantially evenly spaced across the baseplate 101 in the manner illustrated.

The implant 101 further comprises a plurality of transdermal abutments 102 which are located at an inner edge 111 of the baseplate 101. The transdermal abutments 102 are located and sized so as to protrude convergently transdermally into the interior of the orbit for the affixation of an eye prosthesis thereto.

In the embodiment shown, the transdermal abutments 102 comprise a barrel 104 and a coaxial screw bore 105 for the receipt of corresponding screws therein for the attachment of the eye prosthesis. In this way, releasable connectors may be attached to the transdermal abutments 102 for the reasonable attachment of the eye prosthesis. These connectors may comprise magnetic, clip-type connectors and the like.

The eye prosthesis (not shown) may comprise corresponding attachments along a circumference thereof which correspond in location to the distal ends of the abutments 102 for direct attachment thereto. For example, in embodiments, the eye prosthesis may comprise a plurality of embedded magnets along the circumference thereof which correspond in location to the abutments 102 which may comprise corresponding magnets at distal ends thereof. As such, the eye prosthesis may be quickly releasably attached to the abutments 102 by magnetic attachment.

In the embodiment shown, the transdermal abutments 102 comprises three transdermal abutments comprising a top, bottom and central abutment 102. The transdermal abutments 102 stand substantially perpendicularly from the inner edge 111 of the baseplate 101, thereby orientated substantially towards a point of convergence within the interior of the orbit.

FIG. 3 illustrates the baseplate 101 comprising a major anterior portion 106 and at least one minor medial/posterior portions 107.

Figure 5:
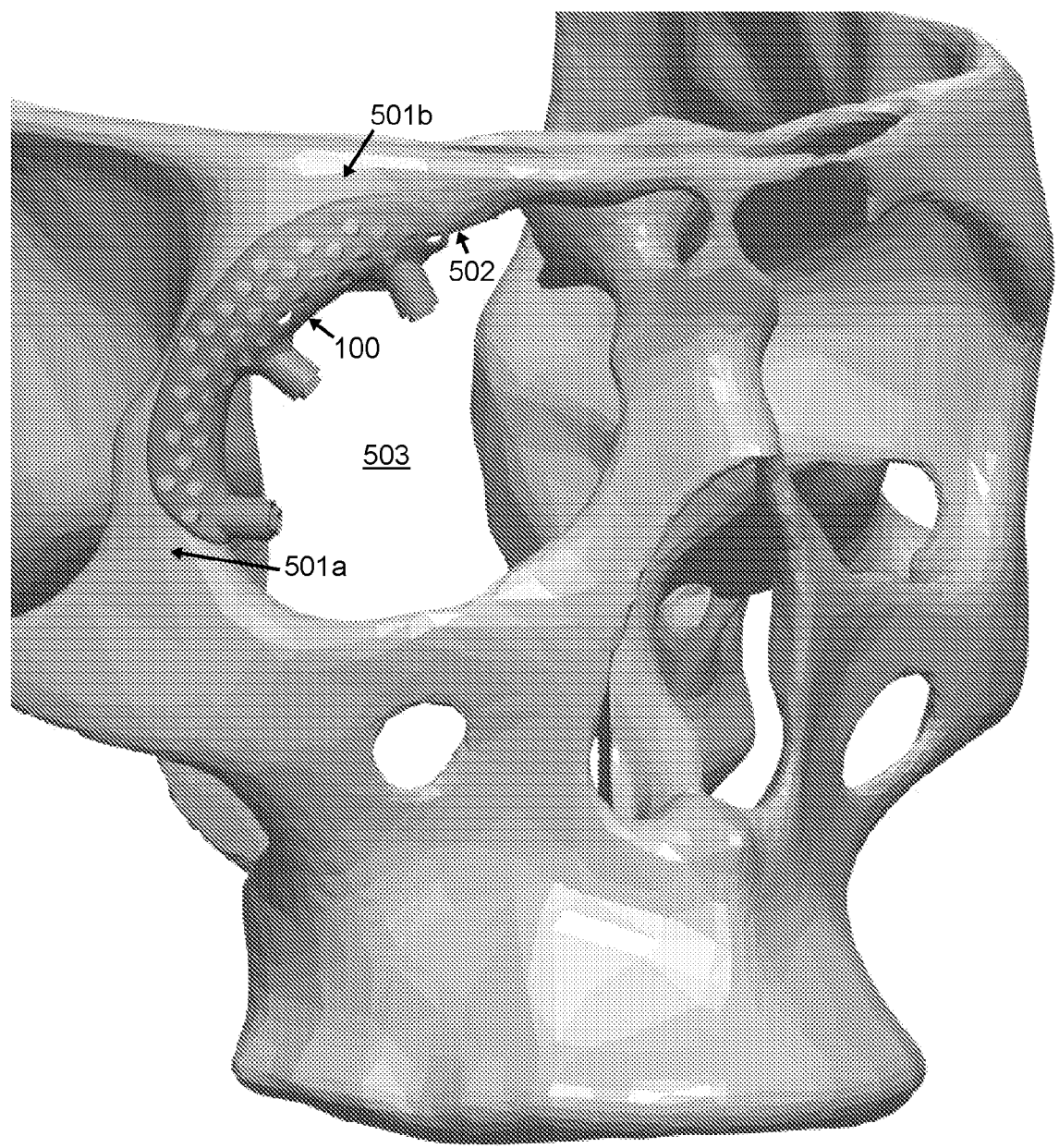
FIGS. 5-7 illustrate the affixation of the implant to the orbital bone.
Figure 6:
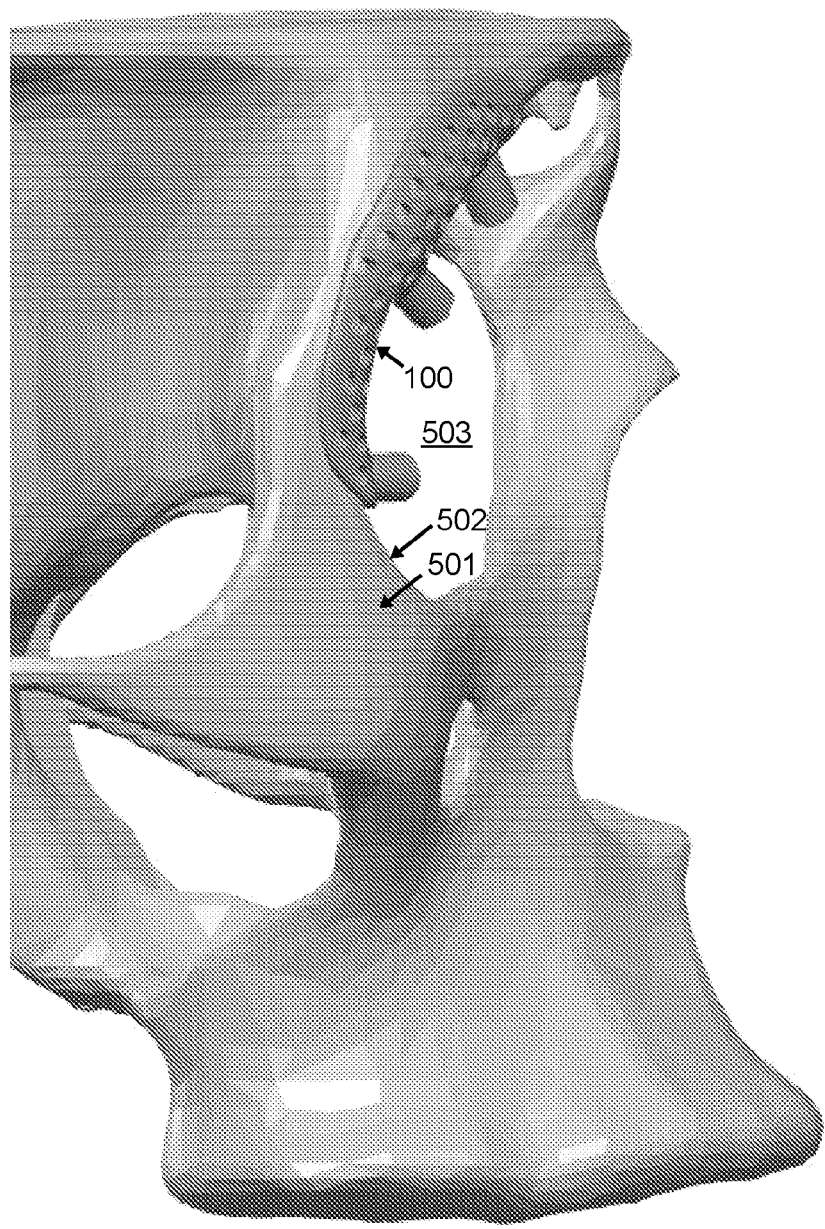
Figure 7:
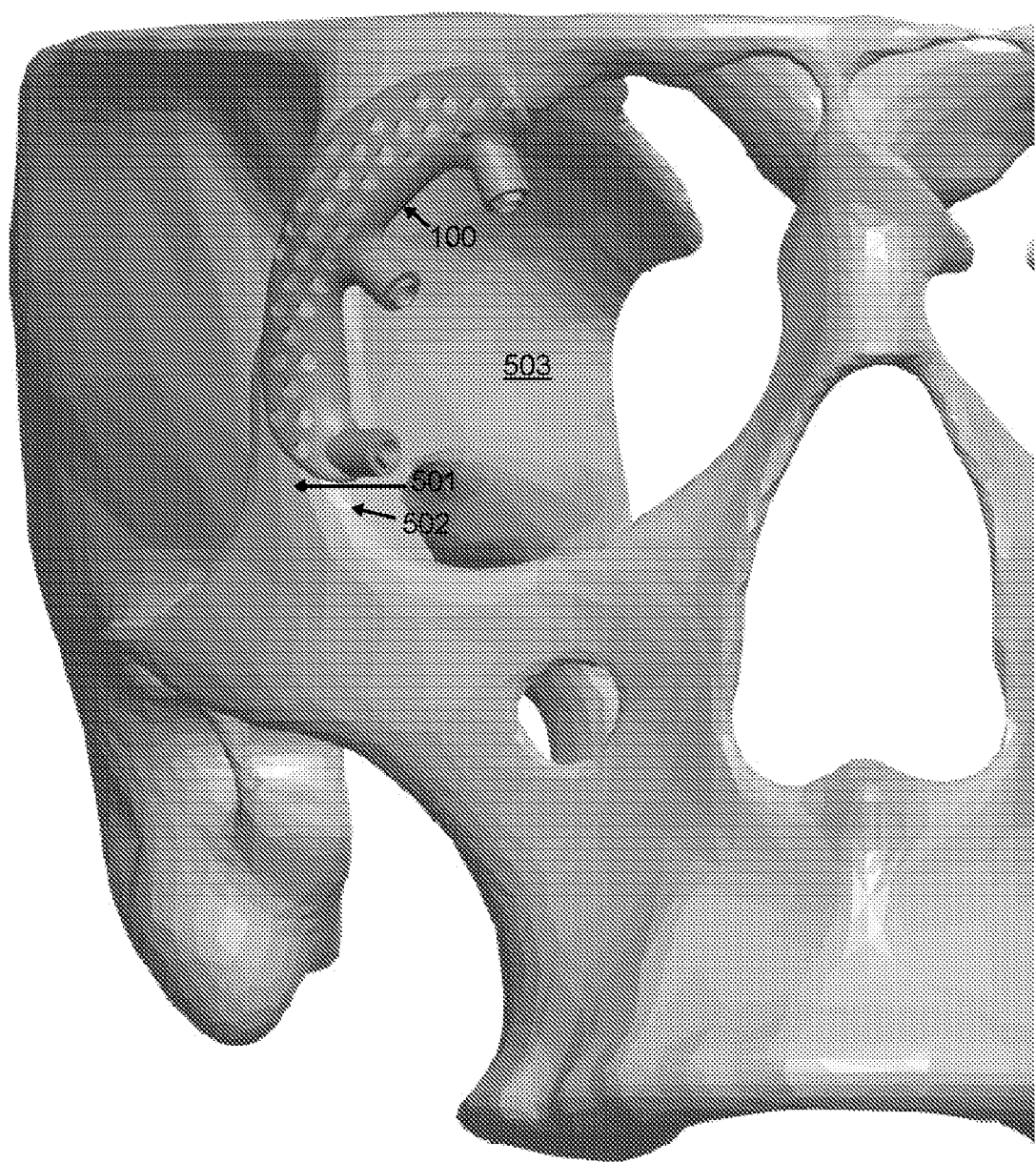

The major anterior portion 106 is of increased size so as to provide a suitable contact surface area against the adjacent wall bone 501 of the orbit 503 as a substantially shown in FIGS. 5-7.

In the example shown in FIGS. 5-7, the implant 100 is attached between the zygomatic bone 501a and the frontal bone 501b at the supero-lateral aspect of the orbit.

In this regard, the microfixation apertures 103 may be located entirely or at least predominantly on the major anterior portion 106 for affixation of microfixation screws to the adjacent wall bone 501.

The minor medial/posterior portions 107 curve posteriorly from the inner edge 111 of the major anterior portion 106 so as to reach and/or reach around the rim 502 of the orbit 503 as is substantially shown in FIGS. 5-7.

As can be appreciated from FIGS. 2 and 3, the minor medial/posterior portions 107 may project at the locations of the transdermal abutments 102 so as to adequately support the bases of the transdermal abutments 102. At locations 108 between the transdermal abutments 102, the minor medial/posterior portions 107 may be receded or be absent.

FIG. 2 illustrates a procedure 200 for the orbit anchored bone affixation of an eye prosthesis using the implant 100 in accordance with an exemplary embodiment.

The procedure 200 may comprise obtaining patient specific geometry at step 201 utilising CT, X-ray or other medical imagery technique.

Step 202 may involve CAD modelling to superimpose a CAD model of the implant 100 against a CAD model of the skull of the patient.

During the CAD modelling, the contouring of the baseplate 101 may be adjusted to conform to the geometry of the adjacent wall 501 and rim 502 bone of the patient's CAD model orbit.

With reference to FIGS. 5-7, the implant 100 is preferably located at a supero-lateral edge of the orbit 503 and therefore the baseplate 101 may be adjusted to the geometry at this location.

The CAD modelling may further comprise the positioning of the transdermal abutments 102 at step 204 during which the transdermal abutments 102 may be placed at the inner edge 111 of the baseplate 101 so as to be substantially perpendicular to the inner edge 101 and orientated substantially towards a point of convergence within the orbit 503.

At step 205, the customised implant 100 CAD model may be 3D printed 205.

At step 206, a physical biomodel of the patient's orbit may also be 3D printed.

As such, at step 207, a prosthetist may construct an eye prosthesis with reference to physically handling the 3D printed replica implant 100 and the physical biomodel of the geometry of the patient's orbit.

Once the prosthesis has been constructed, the titanium implant 100 for implantation may be generated using the customised implant CAD model. As alluded to above, in a preferred embodiment, the implant 100 is manufactured from biocompatible titanium. The transdermal abutments 102 may be polished but the baseplate 101 left roughened to enhance osseointegration.

Thereafter, at step 208, the patient may be placed under general anaesthesia and, at step 209, an incision may be cut at the superior lateral aspect of the orbit 503 to expose the orbit wall 501 and orbit rim 502 bone of the patient.

At step 210, the implant 101 is positioned against the orbit wall 501 and the orbit rim 502 at the location where the customised contouring of the baseplate 101 matches the geometry of the bone.

At step 211, the baseplate 101 is affixed by placing a plurality of microfixation screws (typically 6-10) at chosen locations through the microfixation apertures 103 of the major anterior portion 106.

At step 212, the incision is closed so as to cover the baseplate 101 with surrounding skin, leaving the transdermal abutments 102 protruding transdermally.

At step 213, connectors may be screwed intro the abutments 102 which, as alluded to above, may be magnetic connectors, clip-type connectors, a bar superstructure or the like.

At step 214, the constructed prosthesis is attached to the connectors.

Thereafter, the patient wakes from the anaesthetic having the implant 100 and the prosthesis installed.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A procedure for orbit anchored bone affixation of an eye prosthesis, the procedure comprising: providing an orbital implant, the orbital implant comprising: a baseplate having an orbit radius curvature and an orbit rim curvature and comprising a plurality of microfixation apertures therethrough; and a plurality of transdermal abutments convergently orientated from an inner edge of the baseplate; making an incision to expose a rim of the orbit; attaching the baseplate to the rim; securing the baseplate using a plurality of microfixation screws located through microfixation respective apertures; closing the incision to cover the baseplate while leaving the transdermal abutments exposed; and affixing the eye prosthesis to the transdermal abutments.

2. A procedure as claimed in claim 1, wherein the base plate comprises a major anterior portion and at least one minor medial/posterior portion, the at least one minor medial/posterior portion extending posteriorly from an inner edge of the major anterior portion.

3. A procedure as claimed in claim 2, wherein the microfixation apertures are predominantly located through the major anterior portion.

4. A procedure as claimed in claim 2, wherein the at least one minor medial/posterior portion is located at a respective transdermal abutment.

5. A procedure as claimed in claim 4, wherein the at least one minor medial/posterior portion is at least one of absent or recessed at locations between adjacent transdermal abutments.

6. A procedure as claimed in claim 1, wherein the method comprises affixing between 5 and 11 microfixation screws.

7. A procedure as claimed in claim 1, wherein the plurality of transdermal abutments stand substantially perpendicularly from the inner edge so as to be inwardly convergently orientated.

8. A procedure as claimed in claim 1, wherein the procedure comprises attaching the baseplate at a supero-lateral edge of the orbit between the zygomatic and frontal bones.

9. A procedure as claimed in claim 1, wherein the procedure further comprises obtaining patient geometry and CAD modelling to adjust the shape of the baseplate in conformance with the patient geometry.

10. A procedure as claimed in claim 9 wherein CAD modelling further comprises adjusting positioning of the at least one transdermal abutment according to the patient geometry.

11. A procedure as claimed in claim 9, wherein the procedure further comprises generating a physical biomodel of the orbit and generating the implant or a replica thereof and constructing an eye prosthesis with reference to physical handling of the physical bio model and the implant or the replica thereof.

12. A procedure as claimed in claim 1, wherein the procedure further comprises attaching connectors to the transdermal abutments and attaching the prosthesis using the connectors.

13. A procedure as claimed in claim 12, wherein the eye prosthesis comprises a plurality of attachments along a circumference thereof which correspond in location to distal ends of the transdermal abutments.

14. A procedure as claimed in claim 13, wherein the transdermal abutments comprise more than two transdermal abutments.

15. A procedure as claimed in claim 13, wherein the transdermal abutments comprise three transdermal abutments.

16. A procedure as claimed in claim 15, wherein the connectors are releasable connectors for releasable connection of the prosthesis.

17. A procedure as claimed in claim 16, wherein the connectors comprise magnetic connectors.

18. Apparatus comprising an orbital implant for bone anchored affixation of an eye prosthesis, the implant comprising: a baseplate having an orbit radius curvature and an orbit rim curvature and comprising a plurality of microfixation apertures therethrough; and a plurality of transdermal abutments convergently orientated from an inner edge of the baseplate.

19. Apparatus as claimed in claim 18, wherein the base plate comprises a major anterior portion and at least one minor medial/posterior portion, the at least one minor medial/posterior portion extending posteriorly from an inner edge of the major anterior portion.

20. Apparatus as claimed in claim 19, wherein the microfixation apertures are predominantly located through the major anterior portion.

21. Apparatus as claimed in claim 19, wherein the at least one minor medial/posterior portion is located at a respective transdermal abutment.

22. Apparatus as claimed in claim 19, wherein the at least one minor medial/posterior portion is at least one of absent or recessed at locations between adjacent transdermal abutments.

23. Apparatus as claimed in claim 18, wherein the plurality of transdermal abutments stand substantially perpendicularly from the inner edge and orientated inwardly towards the orbit.

24. Apparatus as claimed in claim 23, wherein the transdermal abutments are substantially respectively orientated towards a point of convergence within the orbit.

25. Apparatus as claimed in claim 18, wherein the transdermal abutments comprise more than two transdermal abutments.

26. Apparatus as claimed in claim 18, wherein the transdermal abutments comprise three transdermal abutments.

27. Apparatus as claimed in claim 18, further comprising a spherical eye prosthesis comprising a plurality of attachments along a circumference thereof and wherein the plurality of attachments correspond in location to distal ends of the plurality of transdermal abutments.

28. Apparatus as claimed in claim 27, wherein the distal ends of the plurality of transdermal abutments and the attachments magnetically attract.

\* \* \* \* \*